US006440468B1

(12) United States Patent
Quintanilla Almagro et al.

(10) Patent No.: US 6,440,468 B1
(45) Date of Patent: Aug. 27, 2002

(54) METHOD FOR OBTAINING APOLAR AND POLAR EXTRACTS OF CURCUMA AND APPLICATIONS THEREOF

(75) Inventors: Eliseo Quintanilla Almagro; Joaquin Diaz Alperi, both of Alicante (ES)

(73) Assignee: A.S.A.C. Pharmaceutical International, A.I.E., Alicante (ES)

(*) Notice: Subject to any disclaimer, the term of this patent is extended or adjusted under 35 U.S.C. 154(b) by 0 days.

(21) Appl. No.: 08/624,443

(22) PCT Filed: Aug. 3, 1995

(86) PCT No.: PCT/ES95/00097

§ 371 (c)(1),
(2), (4) Date: Oct. 28, 1996

(87) PCT Pub. No.: WO96/03999

PCT Pub. Date: Feb. 15, 1996

(30) Foreign Application Priority Data

Aug. 3, 1994 (ES) ............................................. 9401737
May 11, 1995 (ES) ............................................. 9500912

(51) Int. Cl.$^7$ ................................................ A01N 65/00
(52) U.S. Cl. ..................... 424/756; 424/725; 514/824; 514/825
(58) Field of Search .............................. 424/195.1, 725, 424/756; 514/886, 887, 824, 825

(56) References Cited

U.S. PATENT DOCUMENTS

| 4,263,333 A | * | 4/1981 | Maing et al. ............... 426/540 |
| 4,307,117 A | * | 12/1981 | Leshik ......................... 426/96 |
| 4,537,774 A | * | 8/1985 | Shimizu et al. ........... 424/195.1 |
| 4,554,163 A | * | 11/1985 | Weber ....................... 424/195.1 |
| 4,568,546 A | | 2/1986 | Vicario-Arcos .......... 424/195.1 |
| 4,842,859 A | | 6/1989 | Liu ........................... 424/195.1 |
| 4,906,471 A | | 3/1990 | Liu ........................... 424/195.1 |
| 4,927,805 A | * | 5/1990 | Dolfini et al. ................ 512/27 |
| 5,108,750 A | | 4/1992 | Liu ........................... 424/195.1 |
| 5,120,558 A | * | 6/1992 | Nguyen et al. ............. 426/425 |
| 5,178,735 A | * | 1/1993 | Manabe et al. ............... 203/49 |
| 5,266,344 A | | 11/1993 | Mimura et al. ............. 426/546 |
| 5,433,949 A | * | 7/1995 | Kahleyss et al. ......... 424/195.1 |
| 5,494,668 A | * | 2/1996 | Patwardhan ............. 424/195.1 |
| 5,512,285 A | * | 4/1996 | Wilde ....................... 424/195.1 |

FOREIGN PATENT DOCUMENTS

| DE | 2924345 | 1/1981 |
| EP | 0256353 | 2/1988 |
| EP | 0319058 | 6/1989 |
| EP | 0440885 | 8/1991 |
| EP | 0550807 | 7/1993 |
| EP | 0568001 | 11/1993 |
| FR | 0761734 | 3/1934 |
| FR | 2655054 | 5/1995 |
| JP | 6009479 | * 1/1994 |
| KR | 9205687 | * 7/1992 |
| WO | WO 88/05304 | 7/1988 |
| WO | WO 88/08713 | 11/1988 |

OTHER PUBLICATIONS

Ammon et al. (1991) Planta Med. 57:1–7.
Chandra et al. (1972) Indian J. Med. Res. 60:138–42.
Donatus et al. (1990) Biochem. PHarmacol. 39:1869–75.
Gonda et al. (1991) Chem. Pharm. Bull. 39:441–4.
Kiso et al. (1983) J. Med. Plant Res. 49:185–7.
Kuttan et al. (1985) Cancer Letters 29:197–202.
Nagabhushan et al. (1987) Fd. Chem. Toxic. 25:545–7.
Polasa et al. (1991) Fd. Chem. Toxic. 29:699–706.
Rao et al. (1982) Indian J. Med. Res. 75:574–8.
Rafatullah et al. (1990) J. Ethnopharmacol. 29;25–34.
Shalini et al. (1987) Mol. Cell. Biochem. 77:3–10.
Srinivas et al. (1992) Arch. Biochem. Biophys. 292:617–23.
Srimal et al. (1973) J. Pharm. Pharmac. 25:447–52.
Srivastana et al. (1993) Biomed. Reviews 2:15–29.
Srivastava, K.C. (1989) Prostag. Leuko. & Essent. Fat. Acids 37:57–64.
Tomoda et al. (1990) Phytochem. 29:1083–6.
Yegnanarayan et al. (1976) Indian J. Med.Res. 64:601–8.

* cited by examiner

*Primary Examiner*—Christopher R. Tate
(74) *Attorney, Agent, or Firm*—Klauber & Jackson

(57) ABSTRACT

A process for obtaining the apolar extract comprises: (a) extracting the rhizomes with an organic solvent; (b) filtration and evaporation to dryness of the extract; (c) dissolution of the oleoresin obtained in hot conditions, precipitation while allowing to cool down and filtration of the solid; (d) drying and recrystallizing the solid in order to obtain a product having a purity in curcuminoids higher than 90%. Obtaining the polar extract comprises: (a') extraction of the rhizomes with water at 50–70° C. and (b') filtration and evaporation of the water. Application of the compositions and preparations as catchers of free radicals and antiageing agents, as well as reducing agents to reduce the plasma levels of lipid peroxides in human beings are disclosed.

15 Claims, 2 Drawing Sheets

METHOD FOR OBTAINING APOLAR AND POLAR EXTRACTS OF CURCUMA AND APPLICATIONS THEREOF

TECHNICAL FIELD OF THE INVENTION

The present invention fits in the technical field of the obtainment of plant extracts with different medicinal, cosmetic, dietetic applications, etc.

More especially, the present invention provides a method for obtaining apolar and polar extracts of Curcuma that have important applications as catchers of free radicals and anti-ageing agents.

PRIOR ART OF THE INVENTION

Curcumin and other curcuminoids, such as the essential oils obtained from plant extracts of the Curcuma and in general of the Zingiberaceae family, are useful for the treatment and prophylaxis of different diseases. For example, one can cite: EP568,001 (antiviral agents), EP440,885 (antiinflammatory agents), EP319,058 (against loss of hair), EP256,353 (treatment of malabsorption syndromes), U.S. Pat. No. 5,108,750 U.S. Pat. No. 4,906,471, U.S. Pat. No. 4,842,859 platelet antiaggregation agents and anticholesterol agents); WO88/05304 (against hepatitis B and AIDS), WO88/08713 (treatment of neurological disorders), U.S. Pat. No. 4,568,546 (antivenin agent). The antioxodizing and dyeing properties of curcumin and of the derivatives thereof are also known, thus, they are widely used in the food and cosmetic industries as natural preservatives (U.S. Pat. No. 5,266,344, KK KOBE SEIKO SHO).

On the other hand, it is known that the excess of reactive oxygen and free radicals in tissues produces alterations that can lead to premature ageing of cells and the onset of different diseases. Giving the growing concern for this phenomenon, it is not surprising that there are numerous documents about the preparation of plant extracts with antioxidizing effects, catchers of free radicals and therefore useful in the prevention of ageing of cells. However, in the specific case of *Curcuma longa* extracts the number of documents found is not very large and for the most part they are not patent literature.

Among the bibliographic references of the most interesting patents existing in the data banks, application FR2,655,054 (PACIFIC CHEMICAL) about the cellular protection agents contained in curcuminoids (curcumin, 4-hydroxycinnamoyl (pheruloly)methane, bis (-hydroxycinnamoyl) methane, etc.) obtained from *Curcuma longa,* ascorbic acid and/or dismutase superoxide (DSO) stands out. Curcuminoids have a known antioxidizing effect, as well as ascorbic acid and DSO that carry out a synergic effect.

On the other hand, the antiinflammatory activity of curcuminoids can also result from their antioxidizing activity. In this sense, application EP550,807 (STEIGERWALD ARINEIMITTELWERK) describes *Curcuma longa* preparations useful for the treatment of inflammatory diseases associated with the excess production of leukotrienes and prostagalins (Crohn's disease, bronchial asthma, psoriasis, etc.) According to this document, curcumin carries out its antiinflammatory action on the one hand participating in the reactions of elimination of active oxygen and free radicals and on the other hand by inhibiting the cyclooxygenase and lipooxygenase, enzymes responsible for the synthesis of prostaglandins and leukotrienes respectively.

In connection with the methods of extraction of the polar and apolar fractions of the *Curcuma longa* rhizomes, they are conventional methods that use usual solvents (liquids in normal conditions) or else liquid $CO_2$ or $NO_2$ or in supercritical conditions, which is likewise usual for the extraction of fragrances and essential from plants "Carbon dioxide extracted ingredients for fragrances", Flavours & Fragrances O-5M385P, North Albert Road, Reigate, Surrey RH2 9ER, England.)

However, it is a field of noteworthy interest in which it is still desirable to obtain pure extracts, to discover possible new applications of the same in the medical-pharmaceutical fields, in cosmetics, dietetics, etc.

Along these lines, the present invention provides apolar and polar extracts of *Curcuma longa* with important properties as catchers of free radicals and, consequently, antiageing agents of cells. Likewise, these extracts have shown the capacity to reduce plasma levels of lipid peroxides in humans.

On the other hand, according to the bibliographic data it is known that oxygenated radicals generated in cells are controlled by the cell defense system. The excess generation of such radicals can exceed the protective capacity of the defense system and lead to oxidation of the cell components, proteins, lipids and DNA. These oxidative processes are relevant in the pathogenesis of diseases such as arteriosclerosis and rheumatoid arthritis.

DETAILED DESCRIPTION OF THE INVENTION

Just as it is indicated in the title, the present invention refers to a method for obtaining apolar and polar extracts of Curcuma and the applications of these extracts.

Plants of the Curcuma genus and, especially, *Curcuma longa* are tropical plants known from ancient times that belong to the Zingiberaceae family and they originated in Asia. Dried Curcuma rhizomes were already used in Asia as a spice and textile dye. They were also used in popular medicine to treat stomach ailments.

In the last few years, new pharmacological applications have appeared in the scientific literature: antibacterial activity, antiinflammatory activity, lipid peroxidation capacity, antihepatoxic capacity and antitumorigenic capacity.

Curcuma extracts are yellow pigments called curcuminoids, basically comprised of: curcumin (dipheruloylmethane), demethoxycurcumin (hydroxycinnamoylpheruloyl-methane) and bisdeoxycurcimin (dihydroxycinnamoylmethane).

The method of the present invention, for obtaining the apolar extract of *Curcuma longa* is characterized in that it comprises the following operations:

a) subjecting the previously cut, dried and powdered Curcuma rhizomes to a continuous extraction process for 48 hours, using an organic solvent in a rhizome-:solvent ratio of 1:7 weight/volume, carrying out the process in a stationary system to prevent losses of the solvent, for which purpose the temperature of the extraction boiler is adjusted;

b) filtering the extraction mixture resulting from step (a) and evaporating the solvent from the filtrate obtained at reduced pressure obtaining a characteristic brown colored oleoresin as a dry residue;

c) dissolving the oleoresin resulting from step (b) in hot ethyl acetate, in a proportion of 50% w/w and then letting the solution cool down to room temperature for about 24 hours. An orange-colored precipitate that is separated by filtration appears;

d) drying the filtrate coming from the previous step at reduced pressure to obtain a second oleoresin darker than the previous one, whose curcuminoid content is from 20 to 25%;

e) recrystallizing the resulting precipitate in ethyl acetate 50% (w/w) to obtain a solid with a purity in curcuminoids higher than 90%.

On its part, the method of the present invention for obtaining the polar extract of *Curcuma longa* is characterized in that it comprises the following operations:

a) subjecting the previously cut, dried and powdered *Curcuma longa* rhizomes to an extraction process with water, keeping them in maceration for about 24 hours at a temperature between 50 and 70° C.;

b) filtering the extraction mixture resulting from step (a) and evaporating the water from the filtrate this obtained at reduced pressure to obtain a residue that is a hygroscopic solid corresponding to the polar extract of *Curcuma longa*.

Likewise, the method of the present invention is carried out by supercritical extraction, for which purpose the Curcuma rhizome, previously cut, dried and powdered is extracted with ethanol/$CO_2$ and at a pressure of about 260 bar, to obtain the corresponding apolar extract with a purity in curcuminoids of 90%. The apolar extract thus obtained is identical to the one obtained by extraction with solvents according to what is shown by the spectroscopic and chromatographic data thereof. In the same way, but using water as a cosolvent, the polar extract, whose fine layer chromatography totally coincides with that of the extract obtained by maceration in water indicated above, is obtained.

Preferably, obtainment of the above mentioned apolar extract, by supercritical extraction is carried out in the following conditions:

Drying the cut *Curcuma longa* at a temperature of 50° C.;

Grinding the rhizome into particles between 0.–1 and 1 mm;

Extracting the *Curcuma longa* rhizome using ethanol, modified with a small amount of $CO_2$, as a solvent, at 250 bars and 50° C.;

Extracting the ethanol present in the oleoresin with $CO_2$ at 280 bars and 50° C.;

The apolar and polar extracts of Curcuma thus obtained have a capacity to catch free radicals, specifically, $OH^{\cdot}$ hydroxyl and $O_2^{\cdot}$ superoxide radicals as is shown hereinafter by the studies carried out by the inventors in this regard. Besides, said extracts, as it is also shown hereinafter, have a capacity to reduce the plasma levels of lipid peroxides in human beings. Consequently, they have beneficial effects in pathologies related to cell oxidation such as arteriosclerosis and rheumatoid arthritis.

The present invention also includes compositions and preparations with a capacity to catch free radicals, which are effective against ageing processes, protection of genetic material and antimutagenic capacity. Likewise, it includes compositions and preparations with a capacity to reduce the plasma levels of lipid peroxides.

The cited compositions or preparations contain as active principles the polar or apolar extracts of *Curcuma longa* rhizome obtained by the method of the invention or mixtures of the same, along with pharmaceutical quality excipients suitable for oral administration.

These oral preparations can come in solid form (powder, tablets, dragées, capsules, etc.) or in liquid form (syrups or suspensions).

In accordance with what has been said above, the present inventors show as a protective agent or catcher of free radicals, aside from the apolar extract of *Curcuma longa*, which the curcuminoids are in, the aqueous or polar extract of *Curcuma longa* in which there is no curcumin nor curcuminoid. Besides, the studies carried out by the cited inventors, show that the aqueous extract of *Curcuma longa* is in itself a strong catcher of free radicals, especially superoxide ($O_2^{\cdot}$).

The relative application to the reduction of the plasma levels of lipid peroxides is fundamentally based on the capacity to catch free radicals of the cited extracts.

Within the field of study of ageing, it is necessary to evaluate different variables that belong to the scopes of physiology, biochemistry and psychology. The studies directed towards preventive gerontology have lead to the creation of the profile of biological age and life style, that intend to be a tool that evaluates in the strictest and simplest possible way the most sensitive parameters regarding vital habits such as: Pharmacological treatment, tobacco, alcohol, exercise, sleep, perception of one's own health and stress.

Apart from the life style of the population in general, there are biochemical parameters such as total cholesterol, tricglycerides, glucose, uric acid and HDL/cholesterol, which are considered important in the evaluation of the degree of ageing.

In this sense, due to the large amount of information that it creates, it is interesting to include in the profile of biological age, a biochemical parameter, that can be measured rather easily in peripheral blood: lipid peroxides, resulting from the oxidation by the free radicals derived from oxygen, on the polysaturated fatty acids that form part of the phospholipids of membranes.

This oxidative process frequently exceeds the homeostatic capacity of the cell and there may be an abnormal and uncontrolled oxidation process with massive destruction of the cell membrane. It is known that in homeostasis of peroxidation antioxidants such as beta-carotenes and tocopherols take part. Therefore, it is logical to think that exogenous administration of an antioxidant, can be useful to reestablish this cellular balance.

The present inventors have studied the antioxidizing capacity of pharmaceutical compositions comprised of polar and apolar extracts of *Curcuma longa*, for their action on the serum levels of malonaldehyde (MDA) in human beings, as an indicator of their blocking capacity of the action of free radicals of the cell membrane. The conclusions obtained from this study are the following:

1. *Curcuma longa* is a natural extract that reduces the plasma levels of lipid peroxides, which implies a protective mechanism of the cell membrane.

2. It has no toxicity at all: the intake of *Curcuma longa* for 105 days does not modify the liver and kidney blood tests.

3. The effect at the level of lipid peroxides is rapid: 45 days later a drop of the same was already detected, practically in all decades and in both sexes.

4. The inhibition of lipid peroxides and the catch of free radicals, basic properties of *Curcuma longa* are one of the grounds on which the theories of ageing are based.

EMBODIMENTS OF THE INVENTION

Figure 1:
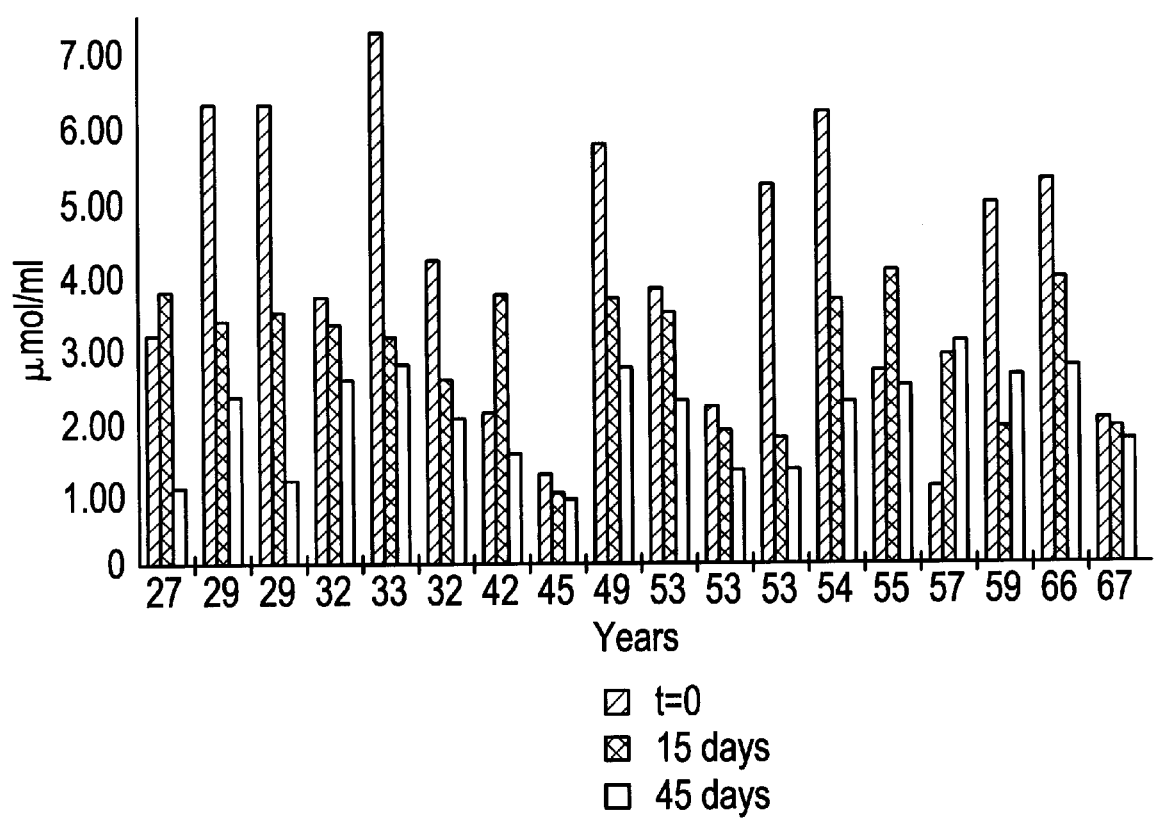
FIG. 1: is a graph presenting values of the lipid peroxide levels for the males of the study.

The present invention is additionally illustrated by the following Examples, which do not have the intention of limiting its scope.

EXAMPLE 1

This example illustrates the obtainment of the apolar extract of Curcuma of the present invention.

13–14 kg. of dry ground Curcuma rhizome were subjected to continuous extraction using 70 liters of dichloromethane. The temperature of the boiler was adjusted until a stationary system was obtained.

Extraction was considered to be finished after 48 hours.

The extract was filtered and the solvent evaporated at reduced pressure (0.5 torr) until it was totally eliminated.

The oleoresin yield using this method varied between 12–15% based on the weight of the starting dry rhizome.

The oleoresin thus obtained was dissolved in hot ethyl acetate (50% by weight) and was left at room temperature for 24 hours, during the course of which an orange-colored precipitate (curcuminoids) that was separated by filtration, appeared little by little.

The filtrate was dried at reduced pressure until a second oleoresin darker than the previous one whose curcuminoid content varied between 20% and 25% was obtained. The precipitate was recrystallized in ethyl acetate (50% by weight) following the above mentioned steps, thus obtaining curcuminoids with a purity higher than 90%.

EXAMPLE 2

This example illustrates the obtainment of the polar extract of Curcuma of the present invention.

30 kg. of ground *Curcuma longa* rhizomes were extracted with 300 liters of water at 70° C. in maceration for 24 hours. The solution was filtered through a filtering plate and the solvent was evaporated at reduced pressure (0.5 bar) obtaining 240 gr. of a hygroscopic solid. Yield 8%.

EXAMPLE 3

This example reveals how the extraction process is optimized by using fluids in a supercritical state, studying the following parameters:

Thermal stability of curcuminoids
Study of the extraction temperature
Study of the feed pressure
Study of the particle size
Study of the humidity of the starting matrix
Study of the flow of the supercritical fluid
Study of the use of ethanol as a cosolvent
Extraction by combined techniques As of the experimental results, costs have been evaluated and the optimal method is the one that includes the following steps:

Drying the cut *Curcuma longa* at a temperature of 50° C.
Grinding the rhizome in particles between 0.1 and 1 mm.
Extracting the *Curcuma longa* rhizome using ethanol, modified with a small amount of $CO_2$ as the solvent at 250 bars and 50° C.
Extracting of the ethanol present in the oleoresin with $CO_2$ at 280 bars and 50° C.

The novelty of this techniques lies in the use of ethanol modified with $CO_2$ for extracting *Curcuma longa* and on the other hand this method reduces costs for extracting curcumin in contrast to conventional techniques, extraction with solvents and/or supercritical extraction with carbon dioxide.

This extraction method increases the selectivity of the extraction of curcumin in contrast to other curcuminoids.

Stability in curcumin

The curcumin present in the apolar fraction shows a thermal degradation in terms of time.

The results indicate a loss of curcuminoids as the temperature rises, above all upon exceeding 50° C.

Initially, a greater degradation is produced which is stabilized as of 24–48 hours of exposure. Degradation is kept at 2% for temperatures lower than 50° C. and at 4% at 80° C.

Study of the extraction temperature

The extraction yield at 250 bar with a flow of 3 kg/h of $CO_2$ and a particle size between 0.1 and 1 mm at 35° C., 40° C., 50° C., 55° C. has been studied and the best yields have been obtained at 55° C.

Study of the feed pressure

The extraction yield has been studied at different temperatures (30° C., 40° C., 50° C.) and at different pressures (100 bar, 150 bar, 200 bar, 250 bar) with a flow of 3 kg/h of $CO_2$ and a particle size between 0.1 and 1 mm. For all the temperatures studied, the maximum yield obtained has been at 250 bars of pressure.

Study of the particle size

The extraction yield has been studied at 50° C. 250 bar and a flow of 3 kg/h of $CO_2$ for different particle sizes.

The maximum yield was obtained for particle sizes between 0.1 and 1 millimeter.

Study of the moisture of the starting matrix

The extraction yield from different samples of Curcuma rhizomes with a different degree of humidity (80%, 50%, 8%) has been studied. The highest yield of curcumin is obtained working at a humidity in the starting matrix of 8%, therefore to obtain the apolar fraction the extraction process is carried out with the dehydrated system.

Study of the flow of supercritical fluid

It has been observed that as the flow of solvent reduces, the onset of diffusive effects is delayed, increasing the solubility effect and increasing the extraction yield. On the other hand, excessively small and/or large flows increase the extraction time.

Extraction with ethanol and supercritical carbon dioxide

The curcuminoid yield has been studied by extracting Curcuma with different proportions of cosolvent (ethanol) in $CO_2$.

The highest yield of oleoresin was obtained by using ethanol 96% with 4% $CO_2$, obtaining a yield of oleoresin of 11.42% (with 43% of curcuminoids) which means 98% of the total amount of the oleoresin in the initial product and a yield of 100% of total curcuminoids.

Extraction by combined techniques

From the supercritical extractions as of *Curcuma longa* oleoresins obtained by extraction with a solvent. It was observed that the extraction was very fast at the beginning, but it began to slow down with time by solidification of the oleoresin. This solid had a compact appearance and it was formed by very fine particles.

As the main component the extract had the solvent used in the extraction.

In these tests the existence of a large cosolvent effect was observed, since the extract obtained was introduced again in the equipment to see if it could be fractionated and it was observed that it was not very soluble in supercritical $CO_2$.

An oleoresin with ethanol and $CO_2$ 96–4% was attained at 250 bar and at 50° C. and then this oleoresin was extracted at 280 bar, 50° C. and using a flow of 3 kg/h of $CO_2$.

The obtained solid oleoresin showed a yield similar to the yield obtained by conventional methods but it increased in the selectivity of the extraction of the oleoresin in the extraction with ethanol in contrast to the extraction with organic solvents. The results are given hereinafter.

|  | Curcumin % | Demethoxy % | Bisdemethoxy % |
|---|---|---|---|
| Oleoresin obtained by conventional methods | 34.50% | 29.50% | 36.00% |
| Oleoresin obtained with EtOH | 72.36% | 17.76% | 9.88% |

Cost estimate

From the above cited studies an estimate of costs has been made studying the different possible cases, calculating the cost per kg of curcumin. The different possibilities are:

a. Starting with *Curcuma longa* and extracting the oleoresin with $CO_2$ in a supercritical state.
   1. Flow of 3 kg/h and apparent density of Curcuma of 0.413 kg/l. Possibility 1.1.
   2. Flow of 3 kg/h and apparent density of Curcuma of 0.573 kg/l. Possibility case 1.2.
   3. Flow of 1 kg/h and apparent density of Curcuma of 0.413 kg/l. Possibility 1.3.

b. Using *Curcuma longa* as the raw material and extracting the oleoresin by a process in batches using a mixture of ethanol/carbon dioxide at a high pressure as the solvent. Possibility 2.

c. Starting with the oleoresin extracted with organic solvents by conventional methods and extracting the solvents present with $CO_2$ in a supercritical state. In this way a solid resin more concentrated in curcumin is obtained. Possibility 3.

d. Starting with an oleoresin extracted with ethanol/$CO_2$ at a high pressure and extracting the ethanol present with $CO_2$ in a supercritical state. In this way a solid oleoresin even more concentrated in curcumin than the previous one is obtained. Possibility 4.

e. Starting with *Curcuma longa* and extracting the oleoresin with $CO_2$ SCX modified with ethanol.
   1. Proportion of ethanol in the solvent of 17%. Possibility 6.1.
   2. Proportion of ethanol in the solvent of 34%. Possibility 6.2.

Operation

In order to carry out the cost estimate, an effectiveness of 90% of the total of the operation has been considered.

It is observed that the most favorable possibility is possibility number 4 wherein the *Curcuma longa* rhizome is extracted with ethanol under pressure and then the oleoresin is purified by extraction with $CO_2$.

Installation

In order to carry out the obtainment of curcumin from its oleoresin, two extractors and two separators, provided with heating jackets, are needed.

The equipment must be equipped with a pump with internal cooling, capable of providing pressures of 300 bar. Besides, a cooler to liquate the $CO_2$ that comes out of the second separator is needed in order to be able to thus recirculate the $CO_2$ lowering operating costs.

The fact of having two extractors is so that a semicontinuous extraction process can be carried out, since during the inoperative times of loading and unloading and pressurizing the unit, the process can continue to operate with the other extractor.

The plant must be equipped with a system to control the pressure and temperature in the extractor and separator and the flow and temperature of the cooler. Besides, a pressure and temperature alarm system must be installed in the extractors, separators and heating jackets, as well as in the cooler in order to prevent any accident.

EXAMPLE 4

This example illustrates a composition in accordance with the present invention, to be administered orally, in the form of tablets comprised of:

| Curcuminoids | 15 mg. |
|---|---|
| Aqueous Curcuma extract | 175 mg. |
| Avicel pH 102 | 489 mg. |
| Starch | 45 mg. |
| Magnesium stearate | 8 mg. |
| Primogel | 3 mg. |
| EM compress | 15 mg. |

EXAMPLE 5

This example illustrates a liquid composition, in accordance with the present invention, to be administered orally, as an emulsion, comprised of:

Curcuminoids 20 mg.

Aqueous Curcuma extract 200 mg.

along with variable amounts of sweeteners (for example, saccharose or fructose) and flavourings (for example, mint or strawberry essence) and of vegetable oils in a sufficient amount for 100 ml. of emulsion.

| Description | Operating conditions | | Us/Ma | S | Operation time | Extracting volume | Volume time 1 | Total cost |
|---|---|---|---|---|---|---|---|---|
| Possibility | P(bar) | T(° C.) | (Kg/h)/Kg | (Kg/Kg) | (h) | (L) | (Lh) | (PTA/Kg) |
| Possibility 1.1 | 250 | 50 | 24.61 | 38 | 1.54 | 24213 | 37288 | 6134 |
| Possibility 1.2 | 250 | 50 | 17.74 | 60 | 3.38 | 17452 | 58988 | 8907 |
| Possibility 1.3 | 250 | 50 | 7.41 | 13 | 1.76 | 24213 | 42615 | 2714 |
| Possibility 2 | 250 | 50 | | 2.16 | 1.47 | 5381 | 7910 | 1061 |
| Possibility 3 | 280 | 50 | 26.95 | 66 | 2.45 | 482 | 1181 | 573 |
| Possibility 4 | 280 | 50 | 26.83 | 33 | 1.23 | 260 | 320 | 164 |
| Possibility 5 | 1 | 80 | 6.10 | 2.53 | 1.50 | 5906 | 8859 | 2103 |
| Possibility 6.1 | 250 | 50 | 25.10 | 60 | 2.39 | 5381 | 12861 | 3696 |
| Possibility 6.2 | 250 | 50 | 23.73 | 20 | 0.89 | 5381 | 4520 | 2222 |

The following examples corresponds to the studies carried out on the extracts of the invention, directed towards determining and evaluating the capacity thereof to catch free radicals, as well as the capacity thereof to reduce lipid peroxides.

EXAMPLE 6

Study of the capacity to catch the superoxide radical ($O_2^-$) by the pyrogallol method Self-oxidation of pyrogallol after an induction period of 20 seconds and for 2 minutes, time in which the increase of absorbency is linear at 420 nm, has been studied. The inhibition of the self-oxidation of pyrogallol by curcuma extracts is used to determine the capacity to catch the $O_2^-$ radical.

The experiment is carried out at 25° C. The pyrogallol is carried out hydrochloric acid 10 mM. The reaction is started when an air saturated Tris-cacodylic acid buffer, with a pH of 8.2 that contains 1 nM of DTPA pyrrogalol, is added. The DTPA is used as a chelating agent to eliminate possible interferences of ions such as iron, copper or manganese.

For apolar extracts of Curcuma a inhibition percentage of 40.92%±0.002 (p<0.01) at a concentration of 16, 129 μg/mL in curcuminoids was found, while the DSO inhibition is of 95%.

EXAMPLE 7

Study of the capacity to catch the hydroxyl radical (OH⁻) by the DMSO method

Capacity to catch the hydroxyl radical by the DMSO test.

The capacity to catch free hydroxyl radicals (OH⁻) by measurement of the formaldehyde generated during the oxidation of the DMSO; a strong catcher of hydroxyl radicals by the ascorbic acid/$FE^{+3}$, has been studied. Oxidation is set off by the ascorbate and it is catalyzed by the $Fe^{+3}$ at 37° C. The reaction mixture is formed with EDTA (0.1 mM, $FE^{+++}$ EDTA complex (/1:2) (167 μM) DMSO (33 mM), problem extract and phosphate buffer 50 mM pH 7.4 in a final volume of 3 mL.

The ascorbic acid (2 mM) is added and after 30 minutes of incubation at 37° C., the reaction is stopped with 1 mL of trifluoracetic acid 17.5% (w/v), and it is measured in an aliquot of 1.5 mL by spectrophotometry.

The competence between the problem extract and the DMSO by the hydroxyl radical (OH⁻) generated coming from the ascorbic/iron system is used to estimate the catching activity of the hydroxyl radical OH⁻ of the problem substance, expressing it as the percentage of inhibition of the production of formaldehyde.

The protocol used is the following:

| EDTA | Bc μL | C μL | Bp μL | P μL |
|---|---|---|---|---|
| $Fe^{+++}$ EDTA | 250 | 250 | 250 | 250 |
| DMSO | 250 | 250 | 250 | 250 |
| VEHICLE | 500 | 500 | — | — |
| EXTRACT | — | — | 500 | 500 |
| PHOSPHATE BUFFER | 250 | — | — | — |
| ASCORBATE | — | 250 | 250 | 250 |

Tc: Control Target
C: Control
Tp: Problem target
P: Problem

The formaldehyde produced is measured in the previous action by addition of 2 mL of a reactive mixture of ammonium acetate and acetylacetone in a phosphate buffer 50 mM pH 7.4, on an aliquot of 1.5 mL. The mixture is incubated at 58° C. for 5 minutes and then the samples are submerged in an ice bath and the 3,5-diacetyl-1,4dihydrolutin formed at 412 nm is measured.

The results obtained were: for the apolar extract curcuminoid mixture it was 95.13±2.46% (P<0.01, n=6) the concentration of the sample being 16.129 μg/mL.

EXAMPLE 8

Study of the capacity to catch the superoxide radical ($O_2^-$) by the NADH-phenazinemethosulfate-$O_2$-nitrotetrazolium blue (NBT)

The capacity to catch free superoxide radicals by inhibition of the formation of diformaran, a highly colored compound that has a maximum absorption at 560 nm is studied. The reaction mixture is comprised of phosphate buffer 19 mM pH 7.4 NADH (90 μM), NBT (43 μM), extract to be tested (vehicle for the target), pH 5 (2.7 μM), all in a volume of 3.1 mL. The reduction reaction of the NBT is started by adding PMS and it is followed spectrophotometrically, by measuring the absorbency at 560 nm and at 20° C. for 2 minutes to calculate the increase of absorbency by (ΔA/min). The following scheme shows the protocol used:

|  | Bc (μL) | C (μL) | Bp (μL) | P (μL) |
|---|---|---|---|---|
| PHOSPHATE BUFFER | 250 | 250 | 250 | 250 |
| NADH | 100 | 100 | 100 | 100 |
| NBT | 100 | 100 | 100 | 100 |
| EXTRACT | — | — | 100 | 100 |
| VEHICLE | 100 | 100 | — | — |
| PMS | — | 100 | — | 100 |

Tc: Control target
C: Control
Tp: Problem target
P: Problem

The percentages of inhibition are obtained for the polar extract of Smilax Lundeli for 5 samples with a concentration of 500 μg/mL, which is of 99.6±0.1% for p<0.1.

EXAMPLE 9

Study of the capacity to catch the superoxide radical ($O_2^-$) by the Xanthine-Xanthine method The capacity to catch the superoxide radical of the polar fraction of *Curcuma longa* by the xanthine-xanthine oxidase method has been studied and there has been an inhibition of 77.95% for a final concentration of 1.25 μg/mL in curcuminoids. It has been verified that the extract does not inhibit the enzyme, which indicates that this extract is a strong catcher of superoxide radicals.

EXAMPLE 10

Study of the effects of the *Curcuma longa* extracts on the levels of lipid peroxides in human blood This example intends to show the action, on the plasma levels of lipid peroxides, of a pharmaceutical composition comprised of polar and apolar extracts of *Curcuma longa*, when it is administered orally, in the form of two tablets daily containing 7 to 14 mg. of curcumin per tablet and from 150 to 175 mg. of aqueous extract of *Curcuma longa,* to a group of healthy subjects of both sexes for a period of two and a half months.

COMPOSITION OF TABLETS OF THE PRESENT EXAMPLE

|  | mg/tablet |
|---|---|
| Apolar extract of *Curcuma longa* | 60* |
| Polar extract of *Curcuma longa* | 175 |
| Avicel pH 102 | 489 |
| Cornstarch | 45 |
| Magnesium stearate | 8 |
| Primogel | 3 |
| EM Compress | 15 |

*Equivalent to 12.5 mg. of Curcuminoids

METHOD

A population of 19 males and 12 females of ages between 27 and 74 years old has been studied, just as it is indicated in the following Table 1:

TABLE 1: Number of subjects studied distributed by ages and sex

| Ages | Frequency |
|---|---|
| Men | |
| 25–30 | 3 |
| 31–40 | 3 |
| 41–50 | 4 |
| 51–60 | 7 |
| 60–70 | 2 |
| Women | |
| 30–40 | 3 |
| 41–50 | 4 |
| 51–75 | 6 |

Peripheral blood was taken from these subjects for the determination of a complete hemogram, of the parameters of evaluation of liver and kidney function; likewise, the level of lipids and lipid peroxides in serum was determined.

After knowing the results, treatment consisting of two tablets daily of *Curcuma longa* with the following protocol was started: second taking of blood fifteen days after administration, determining the above cited parameters. The protocol follow-up was maintained, repeating the blood tests forty-five and seventy-five days after the study started. After this protocol was completed, a 30-day period rest period during which no tablets were administered took place and afterwards the above cited parameters were determined again.

ANALYTICAL METHODS

The hemogram was carried out in a Technicon H-1 analyzer (USA).

The biochemical parameters were carried out following standardized Boehringer-Mannheim reagents (Germany), with a Hitachi 717 self-analyzer (Japan).

The lipid peroxides were determined with malonaldehyde (MDA) by the Ohkama, Ohishi and Yagi method (Analytical Biochem, 95 351–358 (1979)), modified for serum.

RESULTS

During the protocol the patients did not report any of the following signs: dysphagia, pyrosis, nausea, vomiting, diarrhea or constipation.

No alterations either in the hemogram or in the biochemical parameters were observed in the entire population studied, without any distinction of sex or age. It was observed that the enzymes marking liver function, (GOT, GPT, GGT, alkaline phosphatase) as indicators of toxicity of the product and total direct and indirect bilirubin were not affected during the entire process, as one can see in the following Table 3. Said Table 3 shows the initial and final values of GOT, GPT and alkaline phosphatase distributed by age groups in terms of sex. The average and standard deviation are indicated. The units in said table are the following:

(a) Initial Time=Time 0
(b) Final Time=105 days from the beginning
(c) Reference values for the indicated analytical method:

TABLE 3

| | | GOT | | | | GPT | |
|---|---|---|---|---|---|---|---|
| | VR (C) | INITIAL T. (A) | | FINAL TIME (B) | | VR | INITIAL TIME | | FINAL TIME | |
| MEN | | | | | | | | | | |
| Age | | Average | St. Dev. | Average | St. Dev. | | Average | St. Dev. | Average | St. Dev. |
| 25–30 | 0–30 | 21.3 | 3.1 | 22.3 | 3.1 | 0–40 | 19.0 | 5.2 | 18.3 | 3.5 |
| 31–40 | 0–30 | 24.3 | 10.4 | 20.7 | 4.0 | 0–40 | 23.7 | 6.6 | 19.3 | 4.3 |
| 41–50 | 0–30 | 23.0 | 5.1 | 26.0 | 1.7 | 0–40 | 30.8 | 16.9 | 33.0 | 11.3 |
| 51–60 | 0–30 | 20.0 | 8.0 | 23.0 | 7.7 | 0–40 | 21.0 | 10.7 | 21.8 | 4.0 |
| 60–70 | 0–30 | 21.0 | 2.8 | 23.0 | 4.2 | 0–40 | 20.0 | 5.7 | 17.0 | 4.2 |
| WOMEN | | | | | | | | | | |
| AGE | 0–30 | Average | St. Dev. | Average | St. Dev. | 0–40 | Average | St. Dev. | Average | St. Dev. |
| 30–40 | 0–30 | 21.3 | 11.0 | 27.7 | 18.5 | 0–40 | 27.0 | 26.9 | 32.3 | 34.4 |
| 41–50 | 0–30 | 15.0 | 2.2 | 15.5 | 0.7 | 0–40 | 11.0 | 2.6 | 10.0 | 0.0 |
| 51–75 | 0–30 | 16.7 | 3.0 | 20.0 | 2.8 | 0–40 | 15.7 | 3.0 | 12.0 | 5.7 |

TABLE 3-continued

| | GGT | | | ALKALINE PHOSPHATASE | | | |
|---|---|---|---|---|---|---|---|
| | VR (C) | INITIAL T | FINAL T | VR | INITIAL T | | FINAL T |
| MEN | | | | | | | |
| Age | | Average St. Dev. | Average St. Dev. | | Average St. Dev. | Average St. Dev. |
| 25–30 | 11–50 | 18.3   1.5 | 9.0  13.9 | 98–270 | 179.0  13.9 | 154.0  35.7 |
| 31–40 | 11–50 | 25.0  11.2 | 25.7  18.1 | 98–270 | 129.3  26.0 | 137.5  29.7 |
| 41–50 | 11–50 | 25.3  10.5 | 28.3  33.5 | 98–270 | 129.3  33.5 | 93.8   9.8 |
| 51–60 | 11–50 | 32.2  13.0 | 96.5  48.1 | 98–270 | 160.8  45.3 | 153.3  58.9 |
| 60–70 | 11–50 | 20.5   2.5 | 79.7  19.8 | 98–270 | 111.0  22.6 | 132.0  59.4 |
| WOMEN | | | | | | | |
| AGE | 11–50 | Average St. Dev. | Average St. Dev. | 98–270 | Average St. Dev. | Average St. Dev. |
| 30–40 | 11–50 | 18.7   4.0 | 19.0  13.9 | 98–270 | 135.0  13.9 | 138.7  12.2 |
| 41–50 | 11–50 | 12.3   5.0 | 8.5  29.6 | 98–270 | 123.3  29.6 | 117.5  14.8 |
| 51–75 | 11–50 | 12.8   5.2 | 7.5  61.8 | 98–270 | 160.8  61.8 | 180.5  120.9 |

Figure 2:
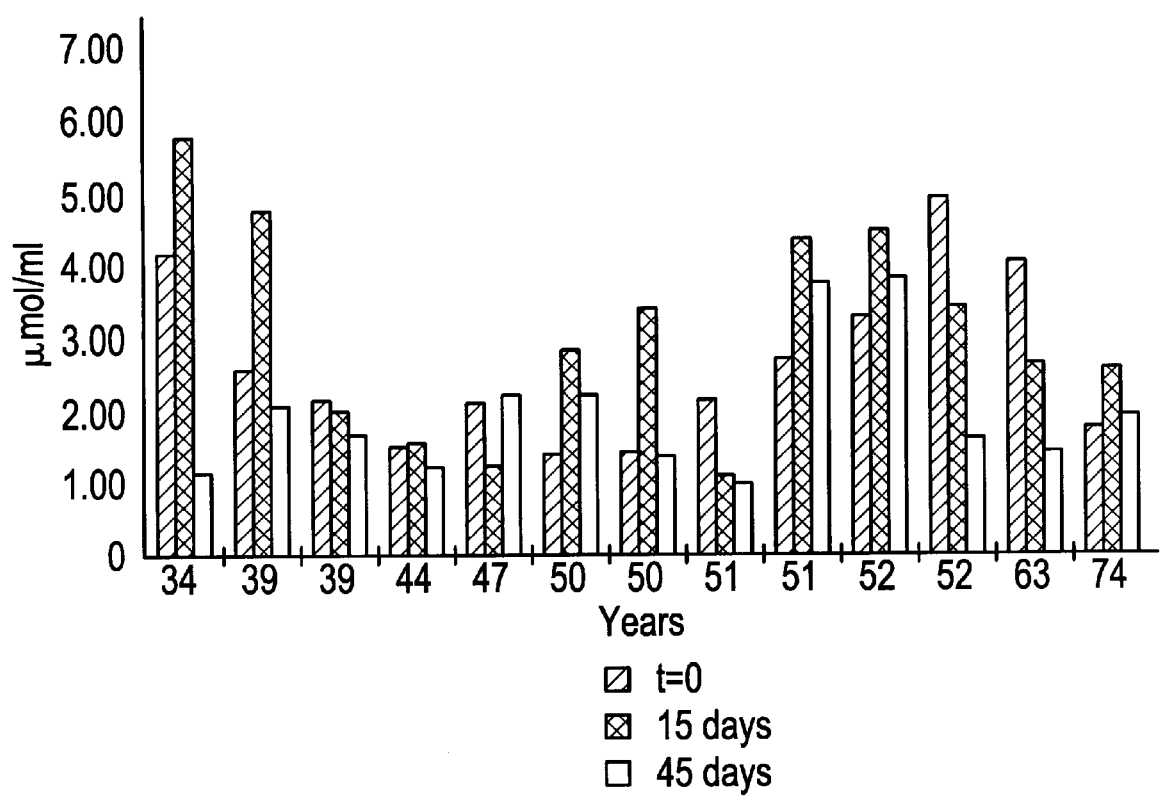
FIG. 2: is a graph presenting values of the lipid peroxide levels for the females of the study.

As is shown in FIG. 1, after 15 days of treatment, a reduction around 8% of the level of lipid peroxides was observed in males, while 45 days after treatment started, the reduction reached an average value of 34%, in such a way that the variation with regard to the situation after 15 days of all of the males subjected to the study will be 59%. In females, an average increase in the level of lipid peroxides (26%) was observed after 15 days (FIG. 2): however, after 45 days, the reduction of the level of peroxides is more evident (it drops an average of 11%), affecting practically all of the subjects; these results imply an average reduction after 45 days with regard to the situation of women subjected to the study after 15 days, of 80%.

What is claimed is:

1. A process for preparing a composition for oral administration, the composition containing an apolar extract and a polar extract from *Curcuma longa* rhizome, said apolar extract has a curcuminoids purity above 90%, and said polar extract is a hygroscopic solid residue that is substantially free of curcuminoids, both of which extracts act in vivo as agents for capturing free radicals in human blood, the process consisting essentially of preparing said apolar extract by subjecting a rhizome powder of *Curcuma longa* rhizomes to a continuous extraction process with an organic solvent in a proportion rhizome powder:organic solvent of 1:7 weight/volume, for a time period of approximately 48 hours, in a stationary system, until obtaining a reaction mixture comprising the extract, filtering the reaction mixture to obtain a first filtrate, evaporating the organic solvent from the first filtrate at reduced pressure until obtaining a dry first residue comprising a first oleoresin of brown color, dissolving said oleoresin in hot ethyl acetate, in a proportion of about 50% w/w to obtain a solution, letting said solution cool down to approximately room temperature for about 24 hours until obtaining an orange-colored precipitate, separating the precipitate by filtration to obtain a second filtrate, drying said second filtrate at reduced pressure until obtaining a second residue comprising a second oleoresin of a darker brown color than said first oleoresin and having a curcuminoid content of 20 to 25%;

recrystallizing said second residue in ethyl acetate at about 50% w/w to obtain the apolar extract;

preparing said polar extract by subjecting a powder of *Curcuma longa* rhizomes to an extraction process by maceration in water for about 24 hours at a temperature between 50 and 70° C., to obtain an extraction mixture;

filtering the extraction mixture to obtain a filtrate and evaporating the water from the filtrate to obtain the polar extract; and mixing the polar and the apolar extracts.

2. A process for preparing a composition for oral administration, the composition comprising an apolar extract and a polar extract from *Curcuma longa* rhizome, wherein said apolar extract has a curcuminoids purity above 90%, and said polar extract is a hygoscopic solid residue that is substantially free of curcuminoids, both of which extracts act in vivo as agents for capturing free radicals in human blood, the process consisting essentially of subjecting ground rhizomes of *Curcuma longa* having a particle size of 0.1 to 1 mm to supercritical extraction, at a pressure of 100 to about 250 bar and a temperature of 30 to about 55° C., with a solvent of $CO_2$-modified ethanol, to obtain an oleoresin;

and extracting said ethanol from said oleoresin with $CO_2$ at 280 bars and 50° C. to obtain said apolar extract having;

preparing said polar extract by a process selected from the group of processes consisting of a first process comprising the steps of subjecting said polar extract by subjecting a powder of *Curcuma longa* rhizomes by maceration in water for about 24 hours at a temperature between 50 and 70° C., to obtain an extraction mixture;

filtering the extraction mixture to obtain a filtrate and evaporating the water from the filtrate to obtain the polar extract;

a second process comprising the steps of subjecting a rhizome powder of *Curcuma longa* rhizomes to a continuous extraction with an organic solvent in a proportion rhizome powder:organic solvent of 1:7 weight/volume, for 48 hours, in a stationary system, until obtaining a reaction mixture comprising the extract, filtering the reaction mixture to obtain a first filtrate, evaporating the organic solvent from the first filtrate at reduced pressure until obtaining a dry first residue comprising a first oleoresin of brown color, dissolving said oleoresin in hot ethyl acetate, in a proportion of 50% w/w to obtain a solution, letting said solution cool down to room temperature for 24 hours until obtaining an orange-colored precipitate, separating the precipitate by filtration to obtain a second filtrate, drying said second filtrate at reduced pressure until obtaining a second residue comprising a second oleoresin of a darker brown color than said first oleoresin and curcuminoid content of 20 to 25%;

recrystallizing said second residue in ethyl acetate at 50% w/w to obtain the solid apolar extract having a curcuminoids purity above 90%, thereby obtaining an apolar extract from *Curcuma longa* rhizome; and mixing the polar and the apolar extracts.

3. A method of capturing free radicals in blood in a mammal in need thereof, the method comprising administering an effective amount of a composition obtained by the process of any of claims 1 or 2.

4. A method of capturing superoxide radicals in a human in need thereof, the method comprising administering to said human an effective amount of a composition obtained by the process of any of claims 1 or 2.

5. A method of reducing plasma levels of lipid peroxides in a human in need thereof, the method comprising administering to said human an effective amount of a composition obtained by the process of any of claims 1 or 2.

6. A method of treating pathologies related to cell oxidation in a manual in need thereof, the method comprising administering to said mammal an effective amount of a composition obtained by the process of any of claims 1 or 2.

7. A method according to claim 6 wherein said pathologies are arteriosclerosis and rheumatoid arthritis.

8. An orally administered composition obtained by the process of any of claims 1 or 2.

9. The composition according to claim 8, whereby the composition is in an amount effective to capture free radicals in blood of a human.

10. The composition according to claim 8, whereby the composition is in an amount effective to capture superoxide radicals in blood of a mammal.

11. The composition according to claim 8, whereby the composition is in an amount effective to reduce plasma levels of lipid peroxides in a human.

12. The composition according to claim 8, whereby the composition is in an amount effective to treat pathologies related to cell oxidation in mammals.

13. The composition according to claim 12, wherein said pathologies are arteriosclerosis or rheumatoid arthritis.

14. The composition according to claim 8, wherein the composition is a solid.

15. The composition according to claim 8, wherein the composition is a liquid.

* * * * *